US012503760B2

(12) United States Patent
Clough et al.

(10) Patent No.: US 12,503,760 B2
(45) Date of Patent: Dec. 23, 2025

(54) METHODS OF USING HIGH-PURITY ALKYNES FOR SELECTIVE DEPOSITION

(71) Applicants: Merck Patent GmbH, Darmstadt (DE); Versum Materials US, LLC, Tempe, AZ (US); Sigma-Aldrich Co.LLC, St. Louis, MO (US)

(72) Inventors: Christopher R. Clough, Plymouth, WI (US); Christopher Jay Thode, Adell, WI (US); Christopher David Hopkins, Carlsbad, CA (US); Sergei V. Ivanov, Schnecksville, PA (US); Agnes Derecskei, Fountain Hills, AZ (US)

(73) Assignees: Merck Patent GmbH, Darmstadt (DE); Sigma-Aldrich Co., LLC, St. Louis, MO (US); Versum Materials US, LLC, Tempe, AZ (US)

( * ) Notice: Subject to any disclaimer, the term of this patent is extended or adjusted under 35 U.S.C. 154(b) by 0 days.

(21) Appl. No.: 18/729,211

(22) PCT Filed: Feb. 23, 2023

(86) PCT No.: PCT/US2023/063089

§ 371 (c)(1),
(2) Date: Jul. 16, 2024

(87) PCT Pub. No.: WO2023/164524

PCT Pub. Date: Aug. 31, 2023

(65) Prior Publication Data

US 2025/0115992 A1 Apr. 10, 2025

Related U.S. Application Data

(60) Provisional application No. 63/268,553, filed on Feb. 25, 2022.

(51) Int. Cl.

| | |
|---|---|
| ***C23C 16/02*** | (2006.01) |
| ***C07C 11/22*** | (2006.01) |
| ***C23C 16/40*** | (2006.01) |
| ***C23C 16/455*** | (2006.01) |

(52) U.S. Cl.

CPC .............. *C23C 16/40* (2013.01); *C07C 11/22* (2013.01); *C23C 16/02* (2013.01); *C23C 16/45525* (2013.01)

(58) Field of Classification Search

CPC ... C23C 16/02; C23C 16/40; C23C 16/45525; C07C 11/22

See application file for complete search history.

(56) References Cited

U.S. PATENT DOCUMENTS

| | | | | |
|---|---|---|---|---|
| 3,829,522 | A * | 8/1974 | Schneider | C07C 1/30 585/905 |
| 2004/0102647 | A1 | 5/2004 | Everett | |
| 2007/0148350 | A1* | 6/2007 | Rahtu | H01L 21/32055 427/249.17 |
| 2012/0045589 | A1* | 2/2012 | Ivanov | C23C 16/405 427/248.1 |
| 2016/0064275 | A1 | 3/2016 | Liu | |
| 2020/0347493 | A1* | 11/2020 | Liu | C23C 16/34 |

FOREIGN PATENT DOCUMENTS

| | | | | |
|---|---|---|---|---|
| CN | 102701896 | * | 10/2012 | C07C 11/24 |
| CN | 112301373 | * | 2/2021 | C25B 3/25 |
| CN | 113563164 | * | 10/2021 | C07C 45/00 |
| DE | DD 240198 A1 | * | 12/1985 | C07C 2/48 |
| FR | 642170 A | | 8/1928 | |
| TW | 200821403 A | * | 3/1996 | C23C 16/18 |
| WO | 2023164524 A1 | | 8/2023 | |

OTHER PUBLICATIONS

Delgado, Salome, et al., "Synthesis and characterization of alkynes β-diketonate copper(I) complexes". Inorganica Chimica Acta, vol. 357, Issue 11, Aug. 5, 2004, pp. 3205-3210.*

International Search Report and Written Opinion, PCT/US2023/063089, mail date Jun. 23, 2023.

Morrison, R.T. and Boyd, R.N., Organic Chemistry, 4th Ed., 558-560, Allyn and Bacon, Inc. Boston, 1983.

Soininen P. J., et al, Journal of The Electrochemical Society, 152, 2,2005, G122-G125.

Aitken, R. Alan et al., A new general synthesis of aliphatic and terminal alkynes: flash vacuum pyrolysis of [beta]-oxoalkylidenetriphenylphosphoranes, Journal of the Chemical Society, Chemical Communications, No. 16, 1985, 1140-1141.

Hampden-Smith, Chemical vapor deposition of metals: Part 2. Overview of selective CVD of Metals, Chemical Vapor Deposition, 1995, 1(2), p. 39-48.

* cited by examiner

*Primary Examiner* — Bret P Chen

(74) *Attorney, Agent, or Firm* — William T. Slaven, IV

(57) ABSTRACT

Methods of using high-purity alkynes substantially free of residual alkyl halides, water and/or carboxylic acids and their use (e.g., in formulations) for enhanced passivation of metallic substrates.

18 Claims, 3 Drawing Sheets

METHODS OF USING HIGH-PURITY ALKYNES FOR SELECTIVE DEPOSITION

CROSS-REFERENCE TO RELATED APPLICATIONS

This application is a national stage application, filed under 35 U.S.C. § 371, of International Patent Application No. PCT/US2023/063089 (filed on 23 Feb. 2023) which claims the benefit of U.S. Provisional Patent Application No. 63/268,553 (filed on 25 Feb. 2022) each of which applications is incorporated herein by reference in their entirety.

BACKGROUND

Field

The disclosed and claimed subject matter relates to high-purity alkynes useful for selective deposition of dielectric films on non-metallic substrates. In particular, the disclosed and claimed subject matter relates to high-purity alkynes and their use for enhanced passivation of metallic substrates.

Related Art

Transition metal-containing films are used in semiconductor and electronics applications. Chemical Vapor Deposition (CVD) and Atomic Layer Deposition (ALD) have been applied as the main deposition techniques for producing thin films for semiconductor devices. These methods enable the achievement of conformal films (metal, metal oxide, metal nitride, metal silicide, and the like) through chemical reactions of metal-containing compounds (precursors). The chemical reactions occur on surfaces which may include metals, metal oxides, metal nitrides, metal silicides, and other surfaces. In CVD and ALD, the precursor molecule plays a critical role in achieving high quality films with high conformality and low impurities. The temperature of the substrate in CVD and ALD processes is an important consideration in selecting a precursor molecule. Higher substrate temperatures, in the range of 150 to 500 degrees Celsius (° C.), promote a higher film growth rate. The preferred precursor molecules must be stable in this temperature range. The preferred precursor is capable of being delivered to the reaction vessel in a liquid phase. Liquid phase delivery of precursors generally provides a more uniform delivery of the precursor to the reaction vessel than solid phase precursors.

CVD and ALD processes are increasingly used as they have the advantages of enhanced compositional control, high film uniformity, and effective control of doping. Moreover, CVD and ALD processes provide excellent conformal step coverage on highly non-planar geometries associated with modern microelectronic devices. CVD and ALD are specifically attractive for fabricating conformal metal containing films on substrates, such as silicon, silicon oxide, metal nitride, metal oxide and other metal-containing layers, using these metal-containing precursors. In these techniques, a vapor of a volatile metal complex is introduced into a process chamber where it contacts the surface of a silicon wafer whereupon a chemical reaction occurs that deposits a thin film of pure metal or a metal compound.

CVD is a chemical process whereby precursors are used to form a thin film on a substrate surface. In a typical CVD process, the precursors are passed over the surface of a substrate (e.g., a wafer) in a low pressure or ambient pressure reaction chamber. The precursors react and/or decompose on the substrate surface creating a thin film of deposited material. Plasma can be used to assist in reaction of a precursor or for improvement of material properties. Volatile by-products are removed by gas flow through the reaction chamber. The deposited film thickness can be difficult to control because it depends on coordination of many parameters such as temperature, pressure, gas flow volumes and uniformity, chemical depletion effects, and time. Thus, CVD occurs where the precursor reacts at the wafer surface either thermally or with a reagent added simultaneously into the process chamber and the film growth occurs in a steady state deposition. CVD can be applied in a continuous or pulsed mode to achieve the desired film thickness.

ALD is a chemical method for the deposition of thin films. It is a self-limiting, sequential, unique film growth technique based on surface reactions that can provide precise thickness control and deposit conformal thin films of materials provided by precursors onto surfaces substrates of varying compositions. In ALD, the precursors are separated during the reaction. The first precursor is passed over the substrate surface producing a monolayer on the substrate surface. Any excess unreacted precursor is pumped out of the reaction chamber. A second precursor or co-reactant is then passed over the substrate surface and reacts with the first precursor, forming a second monolayer of film over the first-formed monolayer of film on the substrate surface. Plasma may be used to assist with reaction of a precursor or co-reactant or for improvement in materials quality. This cycle is repeated to create a film of desired thickness. ALD provides the deposition of ultra-thin yet continuous metal containing films with precise control of film thickness, excellent uniformity of film thickness and outstandingly conformal film growth to evenly coat deeply etched and highly convoluted structures such as interconnect vias and trenches. Thus, ALD is typically preferred for deposition of thin films on features with high aspect ratio.

Thin films, and in particular thin metal-containing films, have a variety of important applications, such as in nanotechnology and the fabrication of semiconductor devices. Examples of such applications include capacitor electrodes, gate electrodes, adhesive diffusion barriers and integrated circuits. However, the continual decrease in the size of microelectronic components, such as semi-conductor devices, presents several technical challenges and has increased the need for improved thin film technologies. In particular, microelectronic components may include features on or in a substrate, which require filling, e.g., to form a conductive pathway or to form interconnections. Filling such features, especially in smaller and smaller microelectronic components, can be challenging because the features can become increasingly thin or narrow. Consequently, a complete filling of the feature, e.g., via ALD, would require infinitely long cycle times as the thickness of the feature approaches zero. Moreover, once the thickness of the feature becomes narrower than the size of a molecule of a precursor, the feature cannot be completely filled. As a result, a hollow seam can remain in a middle portion of the feature when ALD is performed. The presence of such hollow seams within a feature is undesirable because they can lead to failure of the device. Accordingly, there exists significant interest in the development of thin film deposition methods, particularly ALD methods that can selectively grow a film on one or more substrates and achieve improved filling of a feature on or in a substrate, including depositing a metal-containing film in a manner which substantially fills a feature without any voids.

As alluded to above, in conventional semiconductor device fabrication, patterning is a "top-down" process based largely on photolithography and etching, which is a main bottleneck for device downscaling. In contrast, area selective deposition (e.g., CVD and ALD) provides an alternative "bottom-up" method for patterning for advanced semiconductor manufacturing where a metal layer (e.g., Ru) is grown on bottom metal surface (e.g., Ru and TiN) proximate to the passivated dielectric substrate, but not on a dielectric (e.g., $SiO_2$) sidewall. See, e.g., FIG. 1. It is also desirable that these processes be oxygen free and/or have lower resistivity.

In another application it is desired to deposit dielectric film only on another dielectric film but not on metal surface. See, e.g., FIG. 2. One potential application for such process is self-aligned fabrication. Most common strategy to achieve selective growth is based on selective passivation of non-growth surface. Small volatile molecules are highly desired for passivation because they can be supplied via vapor phase. Selective passivation of non-metallic surfaces with high concentration of hydroxyl groups is being widely utilized and includes reaction with various silylating agents, such as $R_xSiCl_y$, $R_xSi(NR_2)_y$, etc. On the other hand, selective passivation of metallic surfaces is much more challenging and selectivity by this approach can be easily lost by desorption of passivating agent and incomplete passivation due to residual impurities on the surface of metal film, etc. Typically, single component reagents are used to passivate non-growth surface. However, single component reagents may not provide complete surface coverage of metal surface due to presence of different sites on the metal surface, such as for example "naked" metal, metal terminated with hydrogen atom, metal terminated with oxygen atom or hydroxyl group, etc.

Alkynes have been used for passivation of metallic surfaces to substantially suppress growth of a film on metallic non-growth surface while depositing the film on a growth dielectric surface. However, previously described alkynes provide insufficient passivation on metal sites due to contamination with traces amounts of moisture, halides and carboxylic acids. Typically, substituted alkynes are prepared by reaction of metal acetylides with alkyl halides, followed up by aqueous workup. See, e.g., Morrison and Boyd, *Organic Chemistry,* 558-560 (1983). Thus, alkynes are contaminated with traces of residual alkyl halides, moisture, and carboxylic acids.

For example, U.S. Patent Application Publication No. 2020/0347493 discloses methods for selective deposition of dielectric films on non-metallic surfaces. The disclosed method requires passivation or blocking of metallic surface prior to deposition of the dielectric films. In some embodiments the method includes treatment of metallic surface with unsaturated hydrocarbons having at least one carbon-carbon triple bond (e.g., 3-hexyne, 4-octyne, 5-decyne, 6-dodecyne and 7-tetradecyne). According to the application, it is believed that the unsaturated hydrocarbons suppress nucleation and growth on the metallic substrate. While the application provides a method to block metallic surface it fails to teach or suggest a process for passivating residual metal oxide sites that are present on the metallic surface.

Reproducible selective passivation of metallic surface requires careful design of the precursors and deposition processes. Indeed, it is highly desired to reduce and/or eliminate passivation of dielectric surfaces while enhancing passivation of metallic surface. The disclosed and claimed subject matter provides compositions and methods for enhanced passivation and/or blocking of metallic surfaces and enhanced selective deposition of non-metallic surfaces relative to metallic surfaces.

To achieve selective surface growth (i.e., the simultaneous or substantially simultaneous growth and non-growth on different surfaces) during semiconductor manufacturing, it is typically desirable to utilize (i) a metallic surface assumed to be free or substantially free of hydroxyl groups and (ii) a non-metallic surface containing high concentration of hydroxyl groups. Examples of suitable metallic surfaces include, but are not limited to, copper, cobalt, tungsten, molybdenum, nickel, ruthenium, etc. Examples of non-metallic surfaces include, but are not limited to, silicon oxide, low K carbon-doped silicon oxides, silicon nitrides, silicon carbonitrides, and metal oxides such as aluminum oxide, tantalum oxide, hafnium oxide, zirconium oxide, etc. Examples of the films deposited on non-metallic surface include, but are not limited to, silicon oxide, aluminum oxide, tantalum oxide, titanium oxide, hafnium oxide, zirconium oxide, tantalum nitride, titanium nitride, etc. The films are deposited on non-metallic surface by chemical vapor deposition and atomic layer deposition processes discussed above. The precursors useful for deposition of the films include, but not limited to, trimethylaluminum, tetrakis (dimethylamido) titanium, pentakis (dimethylamido) tantalum, tert-butylimido-tris(dimethylamido) tantalum, tert-butylimido-tris(dimethylamido) niobium, etc. Co-reactants include, but are not limited to, water, ammonia.

To achieve selective deposition, the metallic surface must be passivated and be free or substantially free of chemical groups reactive toward precursors and co-reactants used in next process step for film deposition, such as for example ammonia. On the other hand, the reactant used for passivation of metallic surface should not passivate desired growth on the non-metallic surface. The disclosed and claimed formulations are uniquely designed to balance these needs in selective deposition processes.

SUMMARY

The disclosed and claimed subject matter relates to high-purity alkynes substantially free of residual alkyl halides, water and/or carboxylic acids and their use (e.g., in formulations) for enhanced passivation of metallic substrates.

In another embodiment, the disclosed and claimed subject matter includes the use of the above-described formulations in selective CVD deposition processes.

In another embodiment, the disclosed and claimed subject matter includes the use of the above-described formulations in selective ALD deposition processes.

BRIEF DESCRIPTION OF THE DRAWINGS

The accompanying drawings, which are included to provide a further understanding of the disclosed subject matter and are incorporated in and constitute a part of this specification, illustrate embodiments of the disclosed subject matter and together with the description serve to explain the principles of the disclosed subject matter. In the drawings.

DETAILED DESCRIPTION

Figure 1:
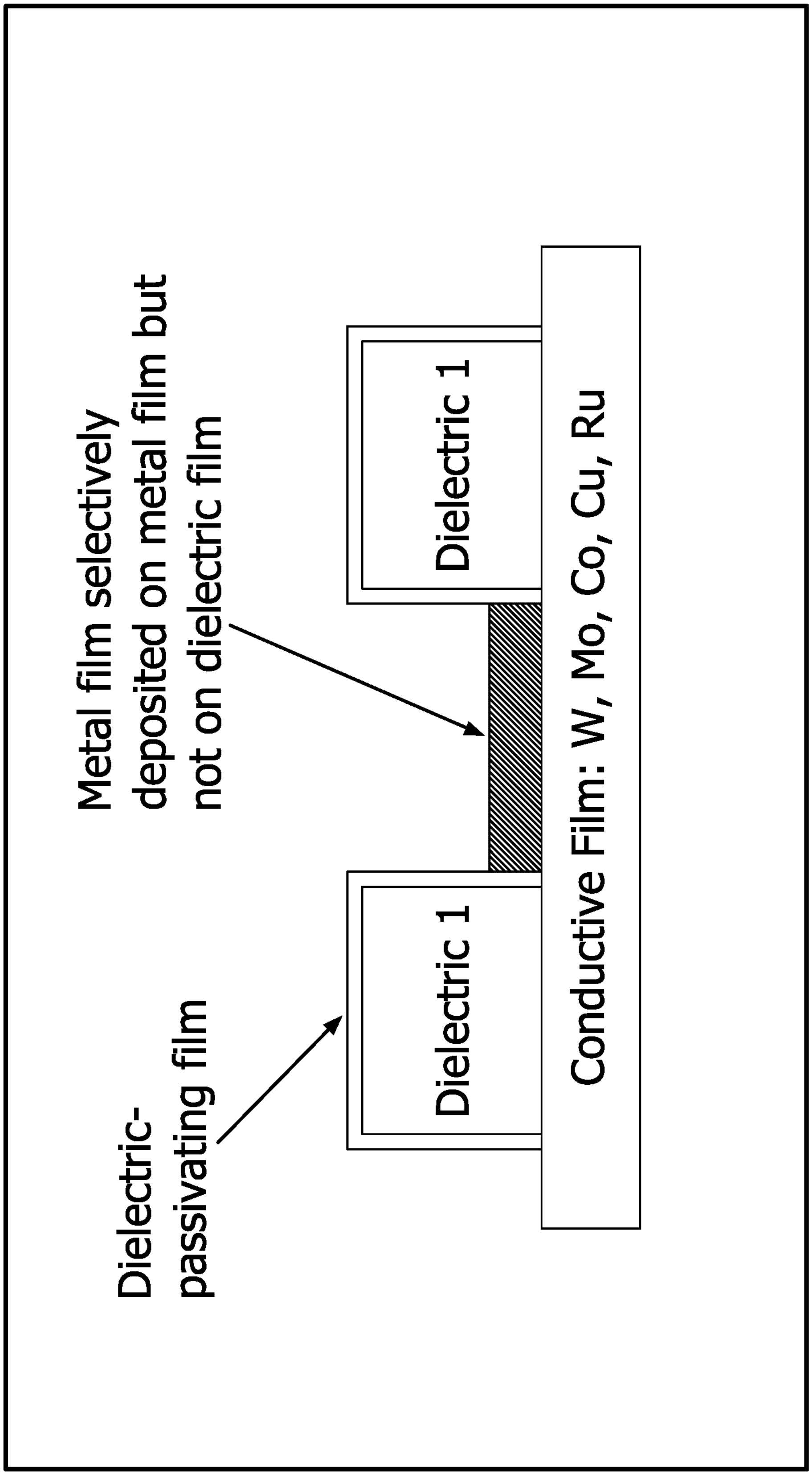
Conventional Art FIG. 1
FIG. 1 illustrates an exemplary target of selective deposition processes where metal film is selectively deposited on conductive film, while dielectric film is passivated.
Figure 2:
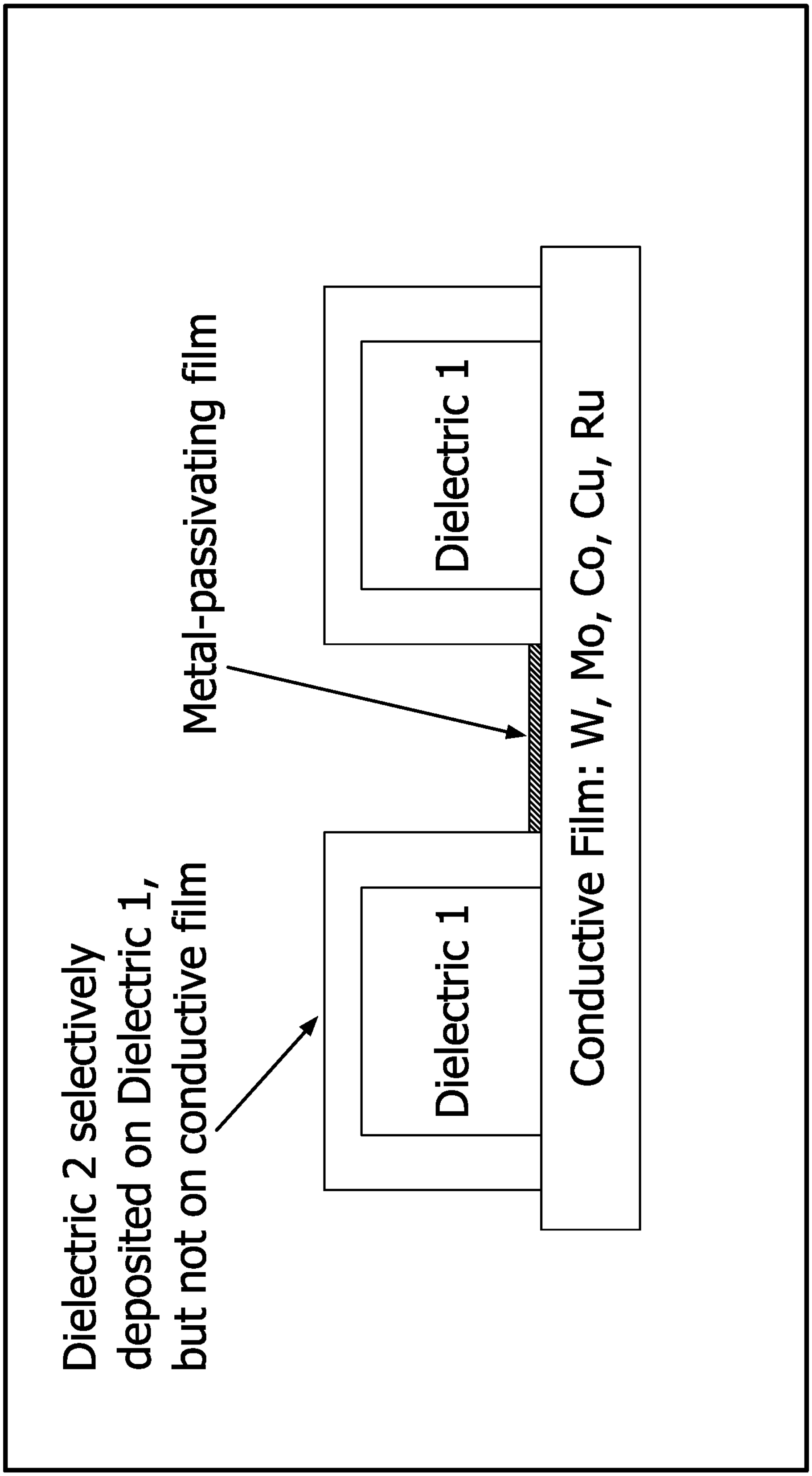
Conventional Art FIG. 2
FIG. 2 illustrates an exemplary target of selective deposition processes where dielectric film is selectively deposited on dielectric film, while metal surface is passivated.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosed and claimed subject matter (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosed and claimed subject matter and does not pose a limitation on the scope of the disclosed and claimed subject matter unless otherwise claimed. No language in the specification should be construed as indicating any non-claimed element as essential to the practice of the disclosed and claimed subject matter. The use of the term "comprising" or "including" in the specification and the claims includes the narrower language of "consisting essentially of" and "consisting of."

Embodiments of the disclosed and claimed subject matter are described herein, including the best mode known to the inventors for carrying out the disclosed and claimed subject matter. Variations of those embodiments may become apparent to those of ordinary skill in the art upon reading the foregoing description. The inventors expect skilled artisans to employ such variations as appropriate, and the inventors intend for the disclosed and claimed subject matter to be practiced otherwise than as specifically described herein. Accordingly, the disclosed and claimed subject matter includes all modifications and equivalents of the subject matter recited in the claims appended hereto as permitted by applicable law. Moreover, any combination of the above-described elements in all possible variations thereof is encompassed by the disclosed and claimed subject matter unless otherwise indicated herein or otherwise clearly contradicted by context.

It will be understood that the term "silicon" as deposited as a material on a microelectronic device will include polysilicon.

For ease of reference, "microelectronic device" or "semiconductor device" corresponds to semiconductor wafers having integrated circuits, memory, and other electronic structures fabricated thereon, and flat panel displays, phase change memory devices, solar panels and other products including solar substrates, photovoltaics, and microelectromechanical systems (MEMS), manufactured for use in microelectronic, integrated circuit, or computer chip applications. Solar substrates include, but are not limited to, silicon, amorphous silicon, polycrystalline silicon, monocrystalline silicon, CdTe, copper indium selenide, copper indium sulfide, and gallium arsenide on gallium. The solar substrates may be doped or undoped. It is to be understood that the term "microelectronic device" or "semiconductor device" is not meant to be limiting in any way and includes any substrate that will eventually become a microelectronic device or microelectronic assembly.

As defined herein, the term "barrier material" corresponds to any material used in the art to seal the metal lines, e.g., copper interconnects, to minimize the diffusion of said metal, e.g., copper, into the dielectric material. Preferred barrier layer materials include tantalum, titanium, ruthenium, hafnium, and other refractory metals and their nitrides and silicides.

"Substantially free" is defined herein as less than 0.001 wt. %. "Substantially free" also includes 0.000 wt. %. The term "free of" means 0.000 wt. %. As used herein, "about" or "approximately" are intended to correspond to within +5% of the stated value.

"Alkylene" means a linear saturated divalent hydrocarbon radical of one to six carbon atoms or a branched saturated divalent hydrocarbon radical of three to six carbon atoms unless otherwise stated (e.g., methylene, ethylene, propylene, 1-methylpropylene, 2-methylpropylene, butylene, pentylene, and the like).

"Heteroalkylene" means an -(alkylene)- radical as defined above where one, two or three carbons in the alkylene chain is replaced by —O—, N(H, alkyl, or substituted alkyl), S, SO, SO2, or CO. In some preferred embodiments, the carbons are replaced by O or N.

In all such compositions, where specific components of the composition are discussed in reference to weight percentage (or "weight %") ranges including a zero lower limit, it will be understood that such components may be present or absent in various specific embodiments of the composition, and that in instances where such components are present, they may be present at concentrations as low as 0.001 weight percent, based on the total weight of the composition in which such components are employed. Note all percentages of the components are weight percentages and are based on the total weight of the composition, that is, 100%. Any reference to "one or more" or "at least one" includes "two or more" and "three or more" and so on.

Where applicable, all weight percents unless otherwise indicated are "neat" meaning that they do not include the aqueous solution in which they are present when added to the composition. For example, "neat" refers to the weight % amount of an undiluted acid or other material (i.e., the inclusion 100 g of 85% phosphoric acid constitutes 85 g of the acid and 15 grams of diluent).

Moreover, when referring to the compositions described herein in terms of weight %, it is understood that in no event shall the weight % of all components, including non-essential components, such as impurities, add to more than 100 weight %. In compositions "consisting essentially of" recited components, such components may add up to 100 weight % of the composition or may add up to less than 100 weight %. Where the components add up to less than 100 weight %, such composition may include some small amounts of a non-essential contaminants or impurities. For example, in one such embodiment, the formulation can contain 2% by weight or less of impurities. In another embodiment, the formulation can contain 1% by weight or less than of impurities. In a further embodiment, the formulation can contain 0.05% by weight or less than of impurities. In other such embodiments, the constituents can form at least 90 wt %, more preferably at least 95 wt %, more preferably at least 99 wt %, more preferably at least 99.5 wt %, most preferably at least 99.9 wt %, and can include other ingredients that do not material affect performance. Otherwise, if no significant non-essential impurity component is present, it is understood that the composition of all essential constituent components will essentially add up to 100 weight %.

The headings employed herein are not intended to be limiting; rather, they are included for organizational purposes only.

As noted above, the disclosed and claimed subject matter relates to high-purity alkynes, substantially free of residual alkyl halides, water, carboxylic acids, and their use (e.g., in formulations) for enhanced passivation of metallic substrates. In particular, it has been discovered that the high-purity alkynes can readily passivate metallic surfaces that are free or substantially free of hydroxyl groups by strong adsorption on "naked" metallic surface. For example, it has been shown that the alkynes strongly adsorb on a "naked" copper surface with an adsorption energy of −40-45 kcal/mol. On the other hand, this behavior was at best inconsistent on partially hydroxylated metallic surfaces; for example, it was also observed that an unsubstituted alkyne did not adsorb well on hydroxylated metallic surface such as copper (I) oxide. Thus, while it is possible to utilize the alkynes on "naked" metallic surfaces, most metal surfaces include residual oxides that would require further processing to render them freely reactive. Thus, it is critical to eliminate impurities which can form hydroxylated metallic surface. It was also discovered that dissociative adsorption of alkyl halides on metallic surfaces is thermodynamically strongly favorable. Residual halides on metallic surface react with precursors and reactants used in selective deposition and suppress process selectivity. Thus, it is critical to eliminate halogen-containing impurities which can form halide-containing species on metallic substrates.

Disclosed and Claimed Formulations

Given the forgoing, in one embodiment the disclosed and claimed subject matter relates to high-purity alkynes substantially free of residual alkyl halides, water and/or carboxylic acids. Preferred high-purity alkynes include those exemplified in Tables 1-3. It is to be understood, however, that the high-purity alkynes are not limited to the to those exemplified in Tables 1-3.

TABLE 1

| Alkyne Structure | |
|---|---|
| 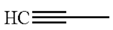 | 1A |
| 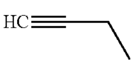 | 1B |
|  | 1C |
| 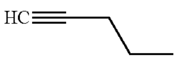 | 1D |
| 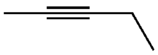 | 1E |

TABLE 1-continued

| Alkyne Structure | |
|---|---|
| 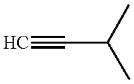 | 1F |
| 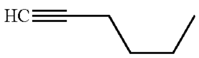 | 1G |
| 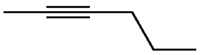 | 1H |
| 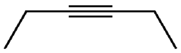 | 1I |
| 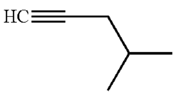 | 1J |
| 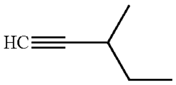 | 1K |
| 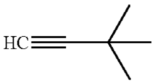 | 1L |
| 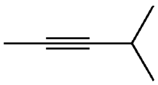 | 1M |
| 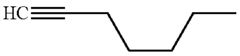 | 1N |
| 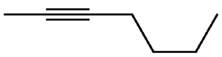 | 1O |
| 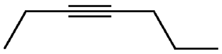 | 1P |
| 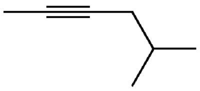 | 1Q |
| 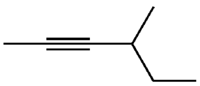 | 1R |
| 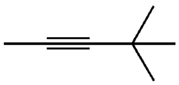 | 1S |
| 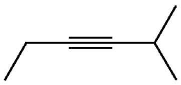 | 1T |
| 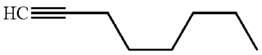 | 1U |

TABLE 1-continued
| Alkyne Structure | |
|---|---|
| 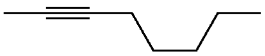 | 1V |
| 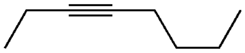 | 1W |
| 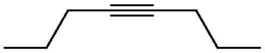 | 1X |
TABLE 2
| Alkyne Structure | |
|---|---|
| 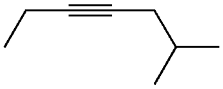 | 2A |
| 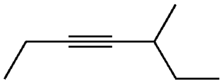 | 2B |
| 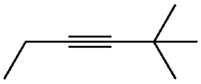 | 2C |
| 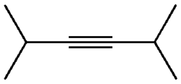 | 2D |
| 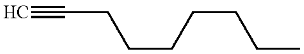 | 2E |
| 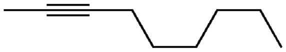 | 2F |
| 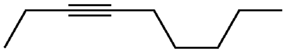 | 2G |
| 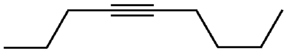 | 2H |
| 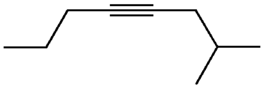 | 2I |
| 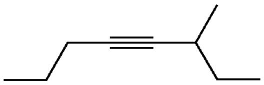 | 2J |
| 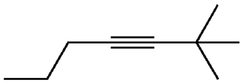 | 2K |
| 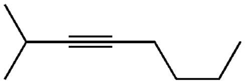 | 2L |
TABLE 2-continued
| Alkyne Structure | |
|---|---|
| 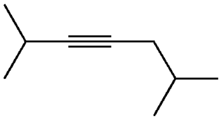 | 2M |
| 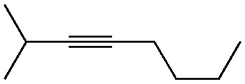 | 2N |
| 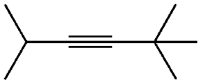 | 2O |
TABLE 3
| Alkyne Structure | |
|---|---|
| 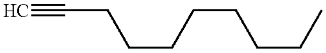 | 3A |
| 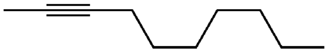 | 3B |
| 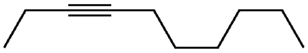 | 3C |
| 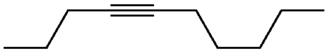 | 3D |
| 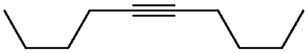 | 3E |
| 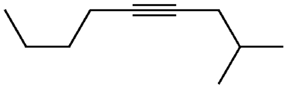 | 3F |
| 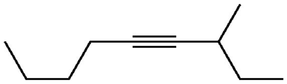 | 3G |
| 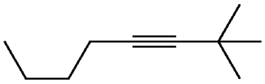 | 3H |
| 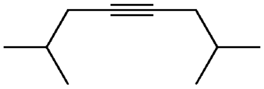 | 3I |
| 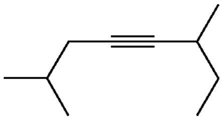 | 3J |

TABLE 3-continued

| Alkyne Structure | |
|---|---|
| 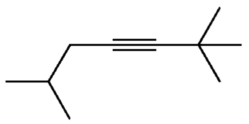 | 3K |
| 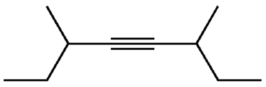 | 3L |
| 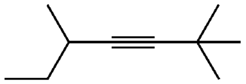 | 3M |
| 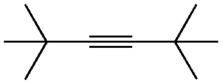 | 3N |

A preferred high-purity alkyne is 5-decyne (3E).

Another preferred high-purity alkyne is 3-hexyne (1I).

In one embodiment, the high-purity alkyne is substantially free of water. In one aspect of this embodiment, the high-purity alkyne has a residual concentration of water of less than about 500 ppm. In one aspect of this embodiment, the high-purity alkyne has a residual concentration of water of less than about 100 ppm. In one aspect of this embodiment, the high-purity alkyne has a residual concentration of water of less than about 50 ppm. In one aspect of this embodiment, the high-purity alkyne has a residual concentration of water of less than about 25 ppm. In one aspect of this embodiment, the high-purity alkyne has a residual concentration of water of less than about 10 ppm. In one aspect of this embodiment, the high-purity alkyne is free of detectable water. In one aspect of this embodiment, the high-purity alkyne is free of water.

In one embodiment, the high-purity alkyne that is substantially free of carboxylic acids. In one aspect of this embodiment, the high-purity alkyne has a residual concentration of carboxylic acids of less than about 1000 ppm. In one aspect of this embodiment, the high-purity alkyne has a residual concentration of carboxylic acids of less than about 500 ppm. In one aspect of this embodiment, the high-purity alkyne has a residual concentration of carboxylic acids of less than about 100 ppm. In one aspect of this embodiment, the high-purity alkyne is free of detectable carboxylic acids. In one aspect of this embodiment, the high-purity alkyne is free of carboxylic acids.

In one embodiment, the high-purity alkyne is substantially free of impurities which may react with metallic surface during a passivation process. In one embodiment, the high-purity alkyne is substantially free of impurities that react with precursors during a deposition process.

In one embodiment, the high-purity alkyne is substantially free of impurities that passivate non-metallic surface and suppress growth on non-metallic surface.

In one embodiment, the high-purity alkyne is substantially free of halogen-containing impurities. In one aspect of this embodiment, the halogen-containing impurities are one or more of a fluorohydrocarbon, a chlorohydrocarbon, a bromohydrocarbon and an iodohydrocarbon. In one aspect of this embodiment, the high-purity alkyne has a residual concentration of halogen-containing impurities of less than about 1000 ppm. In one aspect of this embodiment, the high-purity alkyne has a residual concentration of halogen-containing impurities of less than about 500 ppm. In one aspect of this embodiment, the high-purity alkyne has a residual concentration of halogen-containing impurities of less than about 100 ppm. In one aspect of this embodiment, the high-purity alkyne has a residual concentration of halogen-containing impurities of less than about 50 ppm. In one aspect of this embodiment, the high-purity alkyne has a residual concentration of halogen-containing impurities of less than about 10 ppm. In one aspect of this embodiment, the high-purity alkyne is free of halogen-containing impurities. In the forgoing aspects, the residual concentration of halogen-containing impurities is detected by one or more of the following: Gas Chromatography (GC) and its associated hyphenated techniques comprising but not limited to GC-FID, GC-ECD, GC-MS; Liquid Chromatography (as defined as to encompass LC, HPLC, or UPLC variations) and its associated hyphenated techniques comprising but not limited to LC-DAD and LC-MS; Ion Chromatography (IC) and its associated forms; Spectroscopic techniques comprising but not limited to infrared (IR), Ultraviolet/Visible (UV/Vis), Near infrared (NIR), Raman and Nuclear Magnetic Resonance (NMR) spectroscopies; Inductively Coupled Plasma spectroscopy or spectrometry (ICP) and their associated hyphenated techniques comprising but not limited to ICP-MS, ICP-OES, GC-ICP-MS, and GC-ICP-OES; Elemental analyses such as X-ray fluorescence spectroscopy (XRF) and its associated forms (example WD-XRF) or Atomic Absorbance spectroscopy (AA) and its forms; and finally wet chemical techniques comprising but not limited to Titration (example halogen titration by with silver nitrate) and electrochemical detection (examples, cyclic voltammetry, ion selective electrodes, etc.). In one embodiment of the forgoing aspects, the residual concentration of halogen-containing impurities is detected by one or more of GC-MS, GC-ICP-MS, GC-ICP-OES, GC-FID, GC-ECD, HPLC and UV/Vis.

In one embodiment, the high-purity alkyne is purified by adsorption on alumina. In one aspect of this embodiment the alkyne is passed via adsorption bed packed with acidic alumina. In another aspect of this embodiment, the alkyne is passed via adsorption bed packed with neutral alumina. In another aspect of this embodiment the alkyne is passed via adsorption bed packed with basic alumina. In another aspect of this embodiment the alkyne is passed via adsorption bed including a combination of acidic, basic and neutral alumina.

In one embodiment, the high-purity alkyne is purified by exposure to molecular sieves. In one embodiment, the high-purity alkyne is purified by exposure to silica gel. In one embodiment, the high-purity alkyne is purified by exposure to one or more adsorbent materials.

In one embodiment, the high-purity alkyne is purified by treatment with one or more group (I) metal followed by a distillation process. In one aspect of this embodiment, the alkyne is treated with metallic sodium. In another aspect embodiment, the metal and the alkyne are separated by filtration and the alkyne is distilled to remove non-volatile products of the reaction of impurities with metals.

In one embodiment, the high-purity alkyne is purified by treatment with one or more group (II) metal followed by a distillation process. In one aspect of this embodiment, the alkyne is treated with metallic magnesium. In another aspect embodiment, the metal and the alkyne are separated by filtration and the alkyne is distilled to remove non-volatile products of the reaction of impurities with metals.

In one embodiment, the high-purity alkyne is purified by exposure to activated carbon. In one aspect of this embodiment the alkyne is separated by filtration and is distilled to remove non-volatile products after treatment with activated carbon.

In another aspect of this embodiment, the (i) one or more alkyne is a high-purity alkyne.

Methods of Use

The disclosed and claimed subject matter further includes the use of one or more of the disclosed and claimed high-purity alkynes in chemical vapor deposition process known to those of skill in the art. As used herein, the term "chemical vapor deposition process" refers to any process where a substrate is exposed to one or more volatile precursors, which react and/or decompose on the substrate surface to produce the desired deposition.

In one embodiment, the method includes the use of one or more of the disclosed and claimed high-purity alkynes to passivate metallic surfaces of the substrate and inhibit growth of oxide or nitride films on metallic surfaces in film deposition steps conducted after surface passivation. Metallic surfaces may include, but are not limited to Au, Pd, Rh, Ru, W, Mo, Al, Ni, Cu, Ti, Co, Pt and metal silicides (e.g., $TiSi_2$, $CoSi_2$, and $NiSi_2$). Metal nitride films deposited on pre-passivated metallic substrate may include but are not limited to TaN, TiN, WN, MON, TaCN, TiCN, TaSiN, and TiSiN, and silicon nitride. Metal oxide films deposited on pre-passivated metallic substrate may include but are not limited to $SiO_2$, SiON, $HfO_2$, $Ta_2O_5$, $ZrO_2$, $TiO_2$, $Al_2O_3$, barium strontium titanate and combinations thereof.

When utilized in such deposition methods and processes the high-purity alkynes may be delivered to the reaction chamber such as an ALD reactor in a variety of ways. In some instances, a liquid delivery system may be utilized. In other instances, a combined liquid delivery and flash vaporization process unit may be employed, such as, for example, the turbo vaporizer manufactured by MSP Corporation of Shoreview, MN, to enable low volatility materials to be volumetrically delivered, which leads to reproducible transport and deposition without thermal decomposition of the precursor. The claimed formulations described herein can be effectively used as source reagents via direct liquid injection (DLI) to provide a vapor stream of these metal precursors into an ALD reactor.

When used in these processes, the high-purity alkynes can be combined with and include hydrocarbon solvents which are particularly desirable due to their ability to be dried to sub-ppm levels of water. Exemplary hydrocarbon solvents that can be used in the precursors include, but are not limited to, toluene, mesitylene, cumene (isopropylbenzene), p-cymene (4-isopropyltoluene), 1,3-diisopropylbenzene, octane, dodecane, 1,2,4-trimethylcyclohexane, n-butylcyclohexane, and decahydronaphthalene (decalin). In certain embodiments, the hydrocarbon solvent is a high boiling point solvent or has a boiling point of 100° C. or greater.

A flow of argon and/or other gas may be employed as a carrier gas to help deliver a vapor containing claimed formulations to the reaction chamber during the formulation pulsing. When delivering the high-purity alkynes, the reaction chamber process pressure is between 1 and 100 Torr, preferably between 5 and 20 Torr.

Substrate temperature can be an important process variable in the passivation of metal-containing films. Typical substrate temperatures range from about 150° C. to about 350° C.

In one embodiment, the disclosed and claimed subject matter includes a method for treatment a metallic surface in the presence of at least one other surface that includes the steps of:

a. providing the at least one surface of the substrate in a reaction vessel;
b. forming at least one passivated surface by exposing the at least one surface to one or more of the disclosed and claimed high-purity alkynes.

In step (b) the at least one surface is passivated by exposing the at least one surface to one or more of the disclosed and claimed high-purity alkynes to form a passivating film on the at least one surface. In a further aspect of this embodiment, the method includes depositing a nitride film on the at least one passivated surface. In a further aspect of this embodiment, the method includes depositing an oxide film on the at least one passivated surface.

In one embodiment, the method includes depositing one or more precursors known in the art as a film on the passivating film using an atomic layer deposition process (ALD), including plasma-enhanced ALD (PEALD). As used herein, the term "atomic layer deposition process" or ALD refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous," it is understood that the precursors can be either liquid or solid which are transported with or without an inert gas into the reactor via direct vaporization, bubbling or sublimation. In some case, the vaporized precursors can pass through a plasma generator. The term "reactor" as used herein, includes without limitation, reaction chamber, reaction vessel or deposition chamber.

In a further aspect of this embodiment, the method includes introducing at least one reactant into the reaction vessel where the at least one reactant is selected from the group of water, diatomic oxygen, oxygen plasma, ozone, NO, $N_2O$, $NO_2$, carbon monoxide, carbon dioxide and combinations thereof. In another aspect of this embodiment, the method includes introducing at least one reactant into the reaction vessel where the at least one reactant is selected from the group of ammonia, hydrazine, monoalkylhydrazine, dialkylhydrazine, nitrogen, nitrogen/hydrogen, ammonia plasma, nitrogen plasma, nitrogen/hydrogen plasma, and combinations thereof. In another aspect of this embodiment, the method includes introducing at least one reactant into the reaction vessel where the at least one reactant is selected from the group of hydrogen, hydrogen plasma, a mixture of hydrogen and helium, a mixture of hydrogen and argon, hydrogen/helium plasma, hydrogen/argon plasma, boron-containing compounds, silicon-containing compounds and combinations thereof.

The deposition methods and processes may also involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, and mixtures thereof. For example, a purge gas such as Ar is supplied into the reactor at a flow rate ranging from about 10 to about 2000 sccm for about 0.1 to 10,000 seconds, thereby purging the unreacted material and any byproduct that may remain in the reactor.

The deposition methods and processes require that energy be applied to the at least one of the precursors, oxidizing agent, other precursors or combination thereof to induce reaction and to form the metal-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In some processes, a secondary RF frequency source can be used to modify the plasma characteristics at the substrate surface. When utilizing plasma, the plasma-generated process may include a direct plasma-generated process in which plasma is directly generated in the reactor, or alternatively a remote plasma-generated process in which plasma is generated outside of the reactor and supplied into the reactor.

When utilized in such deposition methods and processes suitable precursors may be delivered to the reaction chamber such as an ALD reactor in a variety of ways. In some instances, a liquid delivery system may be utilized. In other instances, a combined liquid delivery and flash vaporization process unit may be employed, such as, for example, the turbo vaporizer manufactured by MSP Corporation of Shoreview, MN, to enable low volatility materials to be volumetrically delivered, which leads to reproducible transport and deposition without thermal decomposition of the precursor. The precursor compositions described herein can be effectively used as source reagents via direct liquid injection (DLI) to provide a vapor stream of these metal precursors into an ALD reactor.

When used in these deposition methods and processes, precursors can be combined with and include hydrocarbon solvents which are particularly desirable due to their ability to be dried to sub-ppm levels of water. Exemplary hydrocarbon solvents that can be used in the precursors include, but are not limited to, toluene, mesitylene, cumene (isopropylbenzene), p-cymene (4-isopropyltoluene), 1,3-diisopropylbenzene, octane, dodecane, 1,2,4-trimethylcyclohexane, n-butylcyclohexane, and decahydronaphthalene (decalin). In certain embodiments, the hydrocarbon solvent is a high boiling point solvent or has a boiling point of 100° C. or greater. The precursors can also be mixed with other suitable metal precursors, and the mixture used to deliver both metals simultaneously for the growth of a binary metal-containing films.

A flow of argon and/or other gas may be employed as a carrier gas to help deliver a vapor containing precursors to the reaction chamber during the precursor pulsing. When delivering the precursors, the reaction chamber process pressure is between 1 and 50 Torr, preferably between 5 and 20 Torr.

Substrate temperature can be an important process variable in the deposition of high-quality metal-containing films. Typical substrate temperatures range from about 150° C. to about 550° C. Higher temperatures can promote higher film growth rates.

In view of the forgoing, those skilled in the art will recognize that the disclosed and claimed subject matter further includes the use of the disclosed and claimed formulations in chemical vapor deposition (CVD) processes as follows.

In one embodiment, the disclosed and claimed subject matter includes a method for forming a metal-containing film on at least one surface of a substrate that includes the steps of:

a. providing the at least one surface of a substrate in a reaction vessel;
b. forming at least one passivated surface by exposing the at least one surface to one or more of the disclosed and claimed high-purity alkynes; and
c. forming a transition metal-containing film on the at least one pre-passivated surface by a chemical vapor deposition (CVD) process using one or more precursors during the deposition process.

In step (b) the at least one surface is passivated by exposing the at least one surface to one or more of the disclosed and claimed high-purity alkynes to form a passivating film on the at least one surface. In a further aspect of this embodiment, the method includes introducing at least one reactant into the reaction vessel. In a further aspect of this embodiment, the method includes introducing at least one reactant into the reaction vessel where the at least one reactant is selected from the group of water, diatomic oxygen, oxygen plasma, ozone, NO, $N_2O$, $NO_2$, carbon monoxide, carbon dioxide and combinations thereof. In another aspect of this embodiment, the method includes introducing at least one reactant into the reaction vessel where the at least one reactant is selected from the group of ammonia, hydrazine, monoalkylhydrazine, dialkylhydrazine, nitrogen, nitrogen/hydrogen, ammonia plasma, nitrogen plasma, nitrogen/hydrogen plasma, and combinations thereof. In another aspect of this embodiment, the method includes introducing at least one reactant into the reaction vessel where the at least one reactant is selected from the group of hydrogen, hydrogen plasma, a mixture of hydrogen and helium, a mixture of hydrogen and argon, hydrogen/helium plasma, hydrogen/argon plasma, boron-containing compounds, silicon-containing compounds and combinations thereof.

In one embodiment, the disclosed and claimed subject matter includes a method of forming a metal-containing film via a thermal atomic layer deposition (ALD) process or thermal ALD-like process that includes the steps of:

a. providing a substrate in a reaction vessel;
b. forming at least one passivated surface by exposing the at least one surface to one or more of the disclosed and claimed high-purity alkynes;
c. purging the reaction vessel with a first purge gas;
d. introducing into the reaction vessel one or more precursors;
e. introducing into the reaction vessel a source gas;
f. purging the reaction vessel with a second purge gas; and
g. sequentially repeating steps c through f until a desired thickness of the transition metal-containing film is obtained.

In step (b) the at least one surface is passivated by exposing the at least one surface to one or more of the disclosed and claimed high-purity alkynes to form a passivating film on the at least one surface. In a further aspect of this embodiment, the source gas is one or more of an oxygen-containing source gas selected from water, diatomic oxygen, ozone, NO, $N_2O$, $NO_2$, carbon monoxide, carbon dioxide and combinations thereof. In another aspect of this embodiment, the source gas is one or more of a nitrogen-containing source gas selected from ammonia, hydrazine, monoalkylhydrazine, dialkylhydrazine, nitrogen, nitrogen/hydrogen, ammonia plasma, nitrogen plasma, nitrogen/hydrogen plasma and mixture thereof. In a further aspect of this embodiment, the method the first and second purge gases are each independently selected one or more of argon, nitrogen, helium, neon, and combinations thereof. In a further aspect of this embodiment, the method further includes applying energy to the one or more precursor, the source gas, the substrate, and combinations thereof, where the energy is one or more of thermal, plasma, pulsed plasma, helicon plasma, high density plasma, inductively coupled plasma, X-ray, e-beam, photon, remote plasma methods and combinations thereof. In a further aspect of this embodiment, step b of the method further includes introducing into the reaction vessel one or more of the disclosed and claimed formulations using a stream of carrier gas to deliver a vapor of the one or more of the disclosed and claimed formulations into the reaction vessel. In a further aspect of this embodiment, step b of the method further includes use of a solvent medium including one or more of toluene, mesitylene, isopropylbenzene, p-cymene (4-isopropyltoluene), 1,3-diisopropylbenzene, octane, dodecane, 1,2,4-trimethylcyclohexane, n-butylcyclohexane, and decahydronaphthalene (decalin) and combinations thereof.

In one aspect of this disclosure the precursors may be used to co-deposit multi-component oxide films. Multi-component oxide film may include an oxide of two or more elements selected from magnesium, calcium, strontium, barium, aluminum, gallium, indium, titanium, zirconium, hafnium, vanadium, niobium, tantalum, molybdenum, tungsten, tellurium and antimony.

Examples of precursors and co-precursors include but are not limited to trimethylaluminum, tetrakis(dimethylamido) titanium, tetrakis(ethylmethylamino) zirconium, tetrakis (ethylmethylamido) hafnium, pentakis (dimethylamido) tantalum and tris(isopropylcyclopentadienyl) lanthanum.

EXAMPLES

Reference will now be made to more specific embodiments of the present disclosure and experimental results that provide support for such embodiments. The examples are given below to more fully illustrate the disclosed and claimed subject matter and should not be construed as limiting the disclosed subject matter in any way.

It will be apparent to those skilled in the art that various modifications and variations can be made in the disclosed subject matter and specific examples provided herein without departing from the spirit or scope of the disclosed subject matter. Thus, it is intended that the disclosed subject matter, including the descriptions provided by the following examples, covers the modifications and variations of the disclosed subject matter that come within the scope of any claims and their equivalents.

Materials and Methods

All reactions and manipulations described in the examples were conducted under a nitrogen atmosphere using an inert atmosphere glove box or standard Schlenk techniques. Unless indicated otherwise, all reagents were purchased from Sigma-Aldrich and were used "as-is" without further purification. Computer simulation program Dmol3 by Biovia with the M11-L/DNP density functional method was used to calculate and study adsorption characteristics of the disclosed and claimed subject matter. The high-purity alkynes were characterized by Karl Fisher titration, GC-FID and GC-ECD The follow abbreviations are used in the various compositions in the tables below:

| Abbreviation | Full name |
|---|---|
| 5-Decyne | 3E |
| 3-Hexyne | 1I |

SPECIFIC EXAMPLES

Example 1: Adsorption of 5-Decyne on "Naked" Copper Surface

This example evaluated the adsorption of 5-decyne (3E) on "naked" copper surface. It was calculated that 5-decyne strongly chemisorbs on copper (100) surface with an adsorption energy of −43 kcal/mol, and on copper (111) surface with an adsorption energy of −40 kcal/mol.

Example 2: Adsorption of 5-Decyne (3E) on Copper (I) Oxide

This example evaluated the adsorption of 5-decyne (3E) on hydroxyl rich copper (I) and copper (II) oxide. Copper (I) oxide ($Cu_2O$) is a common impurity on metallic copper. The result shows that 5-decyne adsorption on hydroxyl rich $Cu_2O$ is weak (i.e., with an adsorption energy only-6.3 kcal/mol). Accordingly, there is little to no expectation that it will passivate $Cu_2O$ sites on a copper surface. As such, it is critical to minimize and/or eliminate water (and other impurities) in 5-decyne and other alkynes that lead to the formation of $Cu_2O$ sites on copper surfaces resulting in suppression of surface passivation with 5-decyne and other alkynes.

| | Adsorption Energy (kcal/mol) | |
|---|---|---|
| Formulation Component | $Cu_2O$ | CuO |
| 5-Decyne | −6.3 | −15.8 |

Example 3: Adsorption of 1-Bromobutane and Dibromobutane on "Naked" Copper Surface This example evaluated the adsorption of 1-bromobutane and dibromobutane on a "naked" copper surface. 1-bromobutane and dibromobutane are each sometimes used for the synthesis of substituted alkynes. Their use, however, can lead to the presence of residual halogen impurities in the synthesized alkynes. It was calculated that both 1-bromobutane and dibromobutane each strongly chemisorbs on copper (100) surface with an adsorption energy of −21.4 kcal/mol for 1-bromobutane, −24.4 kcal/mol for 1,2-dibromobutane, and −26.1 kcal/mol for 1,4-dibromobutane. The adsorption is dissociative; breaking carbon bromide bonds and resulting in copper surface contaminated with bromide which suppresses passivation of copper surface with alkyne. Thus, high-purity alkyne substantially free of alkyl halides, including alkyl bromides, are desired for selective deposition.

Example 4: Preparation of High-Purity 5-Decyne (3E)

High-purity 5-decyne that is substantially free from water was prepared by recirculating 3 kg of 5-decyne through a column packed with 300 g of 3 Å molecular sieves. Water in 5-decyne before purification was >50 ppm and after purification was 15 ppm, as analyzed by Karl Fisher titration.

Example 5: Preparation of High-Purity 5-Decyne (3E)

High-purity 5-decyne was prepared by distilling 14.4 kg of 5-decyne through a column of Pro-Pak® distillation packing. Purity of 5-decyne was 99.7% before purification and after purification was 99.92%, as analyzed by GC-FID. 1,4-dibromobutane content was 257 ppm before purification and after purification was <1 ppm as analyzed by a combination of GC-FID & GC-ECD. 1-bromobutane content was 72 ppm before purification and after purification was 0.02 ppb as analyzed by a combination of GC-ECD & GC-MS.

Example 6: Comparison of Copper Passivation Using High Purity 5-Decyne (3E) and 5-Decyne (3E) Spiked with Bromobutane In this experiment a sample of high purity 5-decyne and a sample of high purity 5-Decyne spiked with 1,4-dibromobutane were used to study passivation of Cu surface. High purity 5-Decyne was purified by the methods described in the Examples 4 and 5. The amount of residual 1,4-dibromobutane was measured by GC-MS, <1.5 ppm. The sample of purified 5-Decyne was spiked with 1000 ppm of 1,4-bromobutane to produce spiked sample.

PVD Cu coupons from ADVACTIV technology were used for the test. The coupons were loaded into reactor chamber and pre-cleaned from residual surface oxides by treatment with hydrogen gas at 350° C. for 600 sec at 1.75 torr chamber pressure. After this step the copper coupons were exposed to 5-decyne vapor for 180 or 300 seconds at 250° C. In one experiment high purity 5-decyne was used, while in the other experiment 5-decyne spiked with 1,4-bromobutane was used. After the exposure the coupons were transferred into another process chamber without air exposure. The coupons were exposed to 25 ALD cycles to deposit TaN film. Cycle Conditions: 2 sec of pentakis (dimethylamido) tantalum pulse; 20 sec of Ar purge; 7 sec of NH3 pulse; 20 sec of Ar purge. TaN films were deposited at 250° C. wafer temperature and 1 torr chamber pressure.

Figure 3:
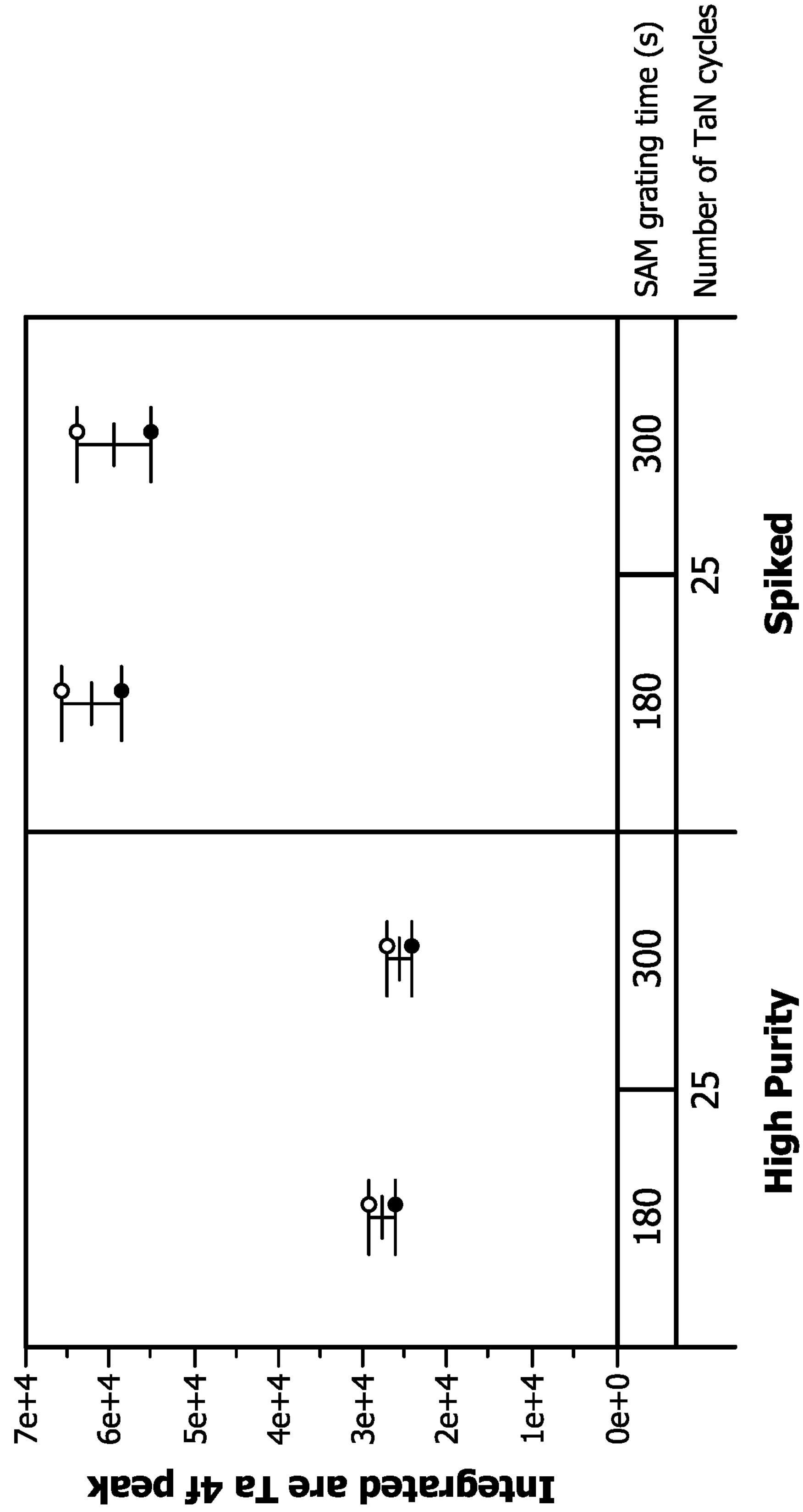
FIG. 3 illustrates the dependence of Ta XPS signal on passivation process conditions, such as purity of the passivating agent (SAM) and exposure time (SAM grating time).

The amount of Ta deposited on Cu surface passivated with high purity 5-decyne and spiked 5-decyne was measured by XPS. FIG. 3 shows the integrated area of Ta XPS peak for two different exposure times (SAM grating time), 180 and 300 sec. In both cases the amount of Ta deposited on Cu surface passivated with high purity 5-decyne was significantly lower compared to the amount of Ta deposited on Cu surface passivated with spiked decyne. The experiment demonstrates that high purity 5-decyne substantially free of haloalkanes (e.g., bromoalkanes) provides significantly better passivation of a Cu surface.

It is anticipated that the disclosed and claimed methods could be used in conjunction with deposition tools commonly found at semiconductor manufacturing sites to produce molybdenum-containing layers for logic applications and other potential functions.

The foregoing description is intended primarily for purposes of illustration. Although the disclosed and claimed subject matter has been shown and described with respect to an exemplary embodiment thereof, it should be understood by those skilled in the art that the foregoing and various other changes, omissions, and additions in the form and detail thereof may be made therein without departing from the spirit and scope of the disclosed and claimed subject matter.

What is claimed is:

1. A method for forming a metal-containing film via a chemical vapor deposition (CVD) process comprising:

a. providing at least one substrate in a reaction vessel;

b. forming at least one passivated surface by exposing at least one surface of the at least one substrate to one or more high-purity alkynes or a formulation thereof, wherein the one or more high-purity alkynes or the formulation thereof has a concentration of halogen-containing impurities of less than about 100 ppm;

c. forming a metal-containing film on the at least one passivated surface using one or more precursors during the deposition process.

2. A method for forming a metal-containing film via a thermal atomic layer deposition (ALD) process comprising:

a. providing at least one a substrate in a reaction vessel;

b. forming at least one passivated surface by exposing at least one surface of the at least one substrate to one or more high-purity alkynes or a formulation thereof, wherein the one or more high-purity alkynes or the formulation thereof has a concentration of halogen-containing impurities of less than about 100 ppm;

c. purging the reaction vessel with a first purge gas;

d. introducing into the reaction vessel one or more precursors;

e. introducing into the reaction vessel a source gas;

f. purging the reaction vessel with a second purge gas; and g. sequentially repeating steps c through f until a desired thickness of a metal-containing film is obtained.

3. The method of claim 1, further comprising depositing a multi-component oxide film on the at least one passivated surface, wherein the multi-component oxide film comprises an oxide of two or more elements selected from magnesium, calcium, strontium, barium, aluminum, gallium, indium, titanium, zirconium, hafnium, vanadium, niobium, tantalum, molybdenum, tungsten, tellurium and antimony.

4. The method of claim 2, further comprising depositing a multi-component oxide film on the at least one passivated surface, wherein the multi-component oxide film comprises an oxide of two or more elements selected from magnesium, calcium, strontium, barium, aluminum, gallium, indium, titanium, zirconium, hafnium, vanadium, niobium, tantalum, molybdenum, tungsten, tellurium and antimony.

5. The method of claim 1, wherein the one or more high-purity alkynes or the formulation thereof has a concentration of halogen-containing impurities of less than about 50 ppm.

6. The method of claim 2, wherein the one or more high-purity alkynes or the formulation thereof has a concentration of halogen-containing impurities of less than about 50 ppm.

7. The method of claim 1, wherein the one or more high-purity alkynes or the formulation thereof has a concentration of halogen-containing impurities of less than about 10 ppm.

8. The method of claim 2, wherein the one or more high-purity alkynes or the formulation thereof has a concentration of halogen-containing impurities of less than about 10 ppm.

9. The method of claim 1, wherein the one or more high-purity alkynes or the formulation thereof has a concentration of water of less than about 50 ppm.

10. The method of claim 2, wherein the one or more high-purity alkynes or the formulation thereof has a concentration of water of less than about 50 ppm.

11. The method of claim 1, wherein the one or more high-purity alkynes or the formulation thereof has a concentration of carboxylic acids of less than about 500 ppm.

12. The method of claim 2, wherein the one or more high-purity alkynes or the formulation thereof has a concentration of carboxylic acids of less than about 500 ppm.

13. The method of claim 1, wherein the one or more high-purity alkynes or the formulation thereof has a concentration of halogen-containing impurities of less than about 10 ppm, a concentration of water of less than about 10 ppm and a concentration of carboxylic acids of less than about 100 ppm.

14. The method of claim 2, wherein the one or more high-purity alkynes or the formulation thereof has a concentration of halogen-containing impurities of less than about 10 ppm, a concentration of water of less than about 10 ppm and a concentration of carboxylic acids of less than about 100 ppm.

15. The method of claim 1, wherein the one or more high-purity alkynes or the formulation thereof comprises one or more of

1A

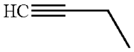
1B

1C

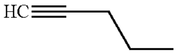
1D

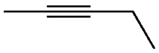
1E

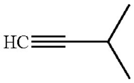
1F

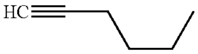
1G

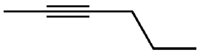
1H

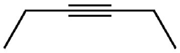
1I

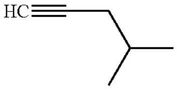
1J

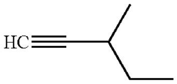
1K

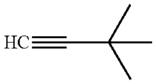
1L

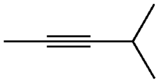
1M

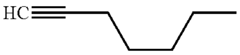
1N

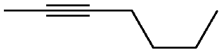
1O

-continued

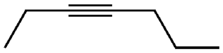
1P

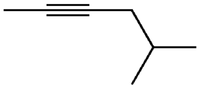
1Q

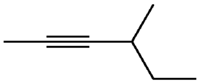
1R

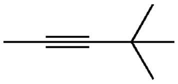
1S

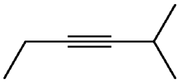
1T

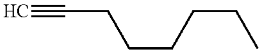
1U

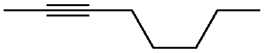
1V

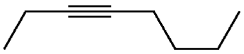
1W

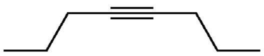
1X

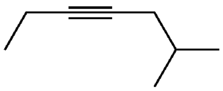
2A

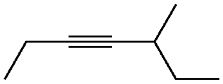
2B

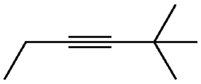
2C

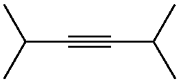
2D

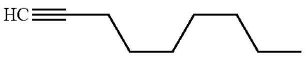
2E

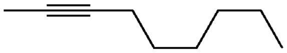
2F

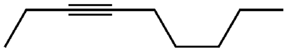
2G

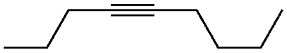
2H

-continued
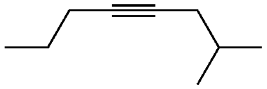
2I
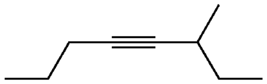
2J
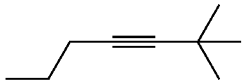
2K
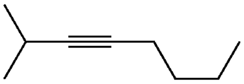
2L
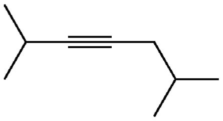
2M
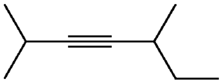
2N
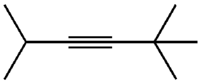
2O
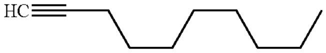
3A
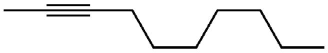
3B
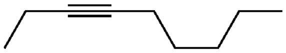
3C
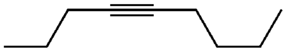
3D
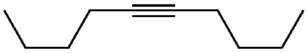
3E
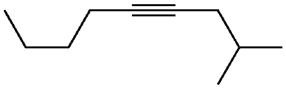
3F
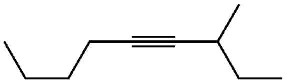
3G
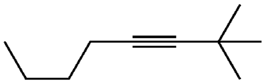
3H
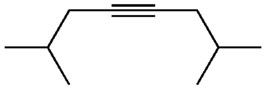
3I
-continued
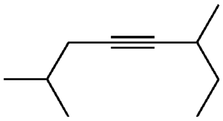
3J
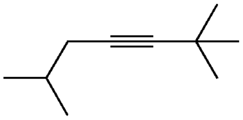
3K
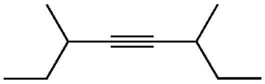
3L
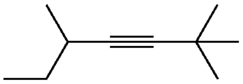
3M
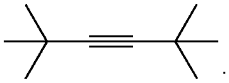
3N
.
16. The method of claim 2, wherein the one or more high-purity alkynes or the formulation thereof comprises one or more of
1A
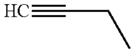
1B
1C
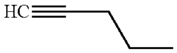
1D
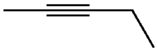
1E
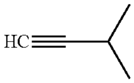
1F
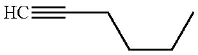
1G
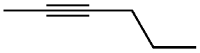
1H
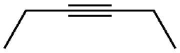
1I
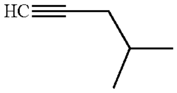
1J
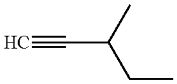
1K -continued
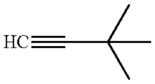
1L
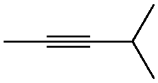
1M
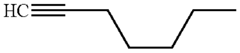
1N
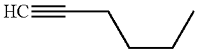
1O
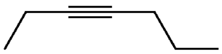
1P
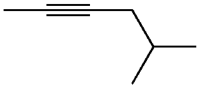
1Q
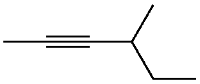
1R
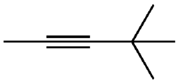
1S
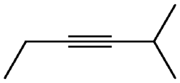
1T
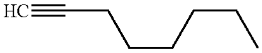
1U
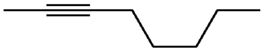
1V
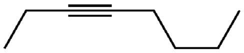
1W
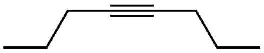
1X
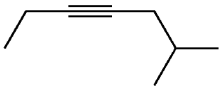
2A
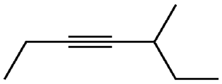
2B
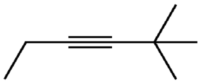
2C
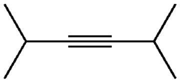
2D
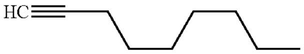
2E
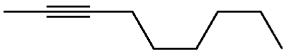
2F
-continued
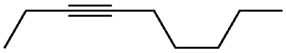
2G
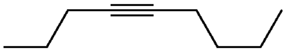
2H
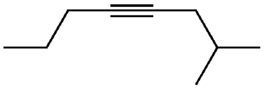
2I
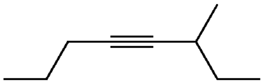
2J
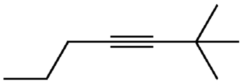
2K
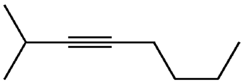
2L
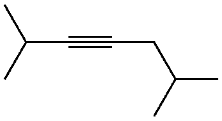
2M
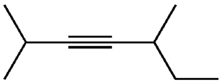
2N
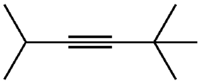
2O
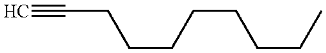
3A
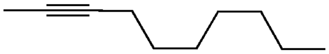
3B
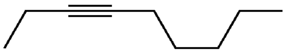
3C
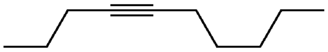
3D
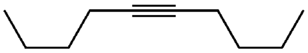
3E
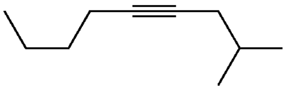
3F
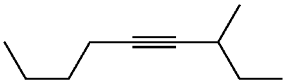
3G
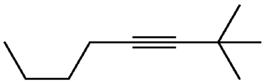
3H -continued

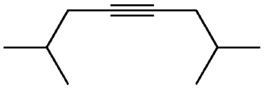

3I

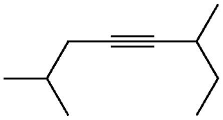

3J

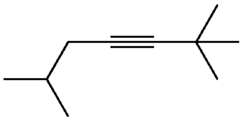

3K

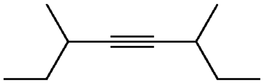

3L

-continued

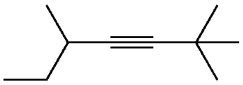

3M

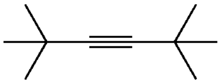

.

3N

17. The method of claim 1, wherein the one or more high-purity alkynes or the formulation thereof comprises one or more of 5-decyne (3E), 1-decyne (3A), 4-octyne (1X), 1-octyne (1U), 3-hexyne (11) and 1-hexyne (1G).

18. The method of claim 2, wherein the one or more high-purity alkynes or the formulation thereof comprises one or more of 5-decyne (3E), 1-decyne (3A), 4-octyne (1X), 1-octyne (1U), 3-hexyne (11) and 1-hexyne (1G).

* * * * *